United States Patent
Chuang

(10) Patent No.: US 10,149,975 B2
(45) Date of Patent: Dec. 11, 2018

(54) TRANSCUTANEOUS ELECTRICAL NERVE STIMULATION DEVICE

(71) Applicant: Easywell Biomedicals, Inc., HsinChu (TW)

(72) Inventor: Cheng-Lin Chuang, Taoyuan (TW)

(73) Assignee: EASYWELL BIOMEDICALS, INC., Hsinchu (TW)

( * ) Notice: Subject to any disclaimer, the term of this patent is extended or adjusted under 35 U.S.C. 154(b) by 259 days.

(21) Appl. No.: 15/057,315

(22) Filed: Mar. 1, 2016

(65) Prior Publication Data

US 2017/0252561 A1 Sep. 7, 2017

(51) Int. Cl.
| | |
|---|---|
| *A61N 1/05* | (2006.01) |
| *A61N 1/36* | (2006.01) |
| *A61N 1/04* | (2006.01) |
| *A61N 5/06* | (2006.01) |

(52) U.S. Cl.
CPC ....... *A61N 1/36021* (2013.01); *A61N 1/0456* (2013.01); *A61N 5/0622* (2013.01); *A61N 5/0625* (2013.01); *A61N 2005/066* (2013.01); *A61N 2005/0645* (2013.01)

(58) Field of Classification Search
CPC ..... A61N 1/08; A61N 1/0456; A61N 1/36021
See application file for complete search history.

(56) References Cited

U.S. PATENT DOCUMENTS

| | | | |
|---|---|---|---|
| 5,423,874 A | 6/1995 | D'Alerta | |
| 5,450,845 A | 9/1995 | Axelgaard | |
| 6,600,957 B2 | 7/2003 | Gadsby | |
| 7,245,957 B2 | 7/2007 | Rowe et al. | |
| 7,483,738 B2 | 1/2009 | Tamarkin | |
| 8,041,430 B2 | 10/2011 | Lau | |
| 8,260,439 B2 | 9/2012 | DiUbaldi et al. | |
| 8,290,581 B2 | 10/2012 | Kriksunov et al. | |
| 9,114,258 B2 | 8/2015 | Escribano | |
| 2005/0227998 A1 | 10/2005 | Voelker | |
| 2006/0265029 A1 | 11/2006 | Huang et al. | |
| 2014/0207219 A1 | 7/2014 | Dunbar et al. | |
| 2014/0236258 A1 | 8/2014 | Carroll et al. | |
| 2015/0290028 A1 | 10/2015 | Isserow et al. | |
| 2016/0030408 A1* | 2/2016 | Levin | A61B 5/04001 514/330 |
| 2016/0106576 A1* | 4/2016 | Badawi | A61F 13/124 607/109 |

FOREIGN PATENT DOCUMENTS

KR 2014102967 8/2014

\* cited by examiner

*Primary Examiner* — Michael D Abreu
(74) *Attorney, Agent, or Firm* — Birch, Stewart, Kolasch & Birch, LLP

(57) ABSTRACT

A transcutaneous electronic nerve stimulation device configured to provide therapy to a patient includes a control unit assembly, a power source, and a therapy plate electrically coupled to the power source. The therapy plate includes an electrical source configured to deliver electrical stimulation to the patient, a heat source configured to deliver heat to the patient, and a radiation source configured to deliver radiation to the patient. The transcutaneous electronic nerve stimulation device further includes a rigid connector electrically coupling the therapy plate to the power source such that the therapy plate is fixed relative to the power source.

6 Claims, 2 Drawing Sheets

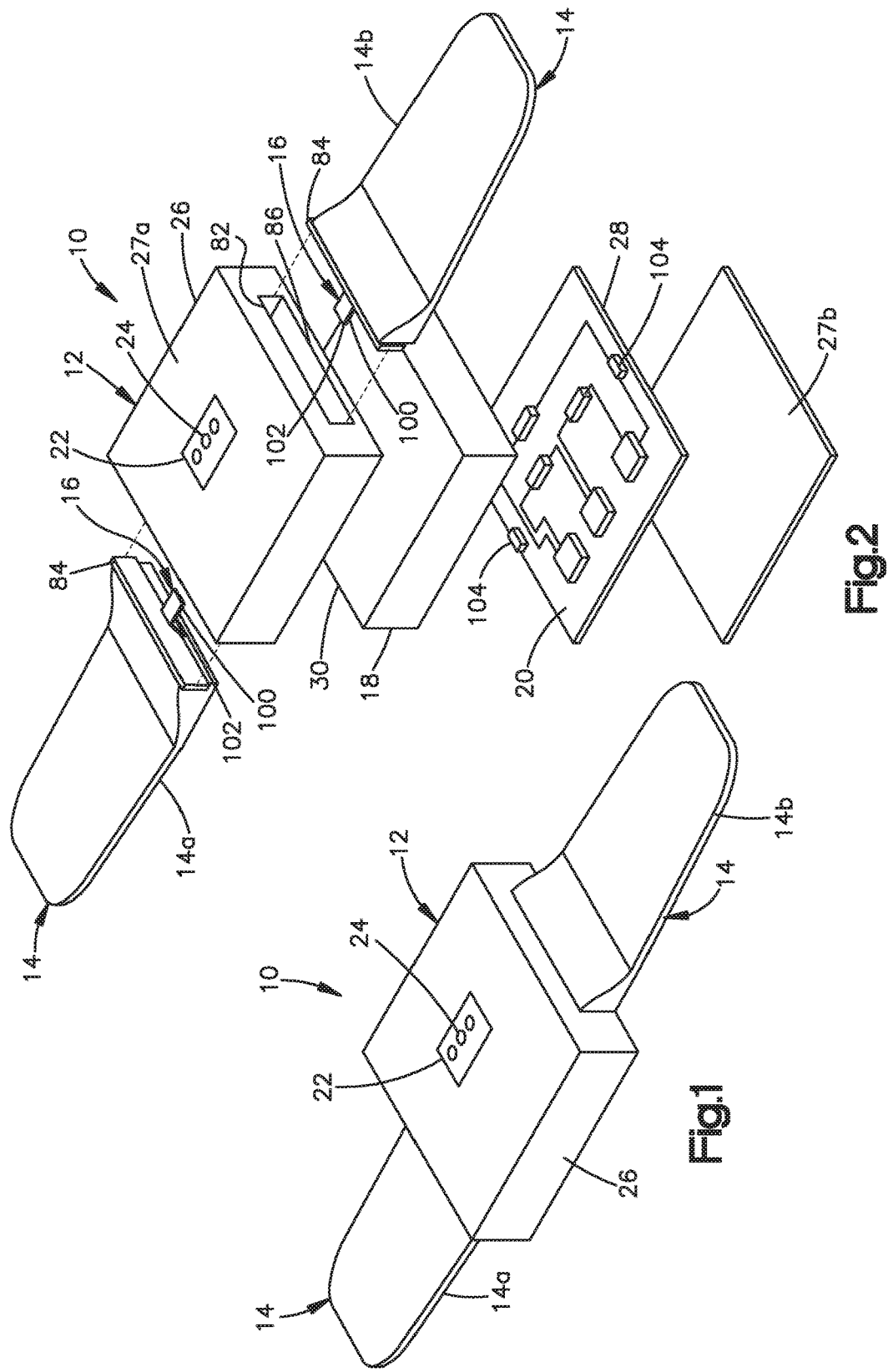

TRANSCUTANEOUS ELECTRICAL NERVE STIMULATION DEVICE

TECHNICAL FIELD

The present application relates generally to devices configured to reduce pain. More specifically, the present application relates to devices configured to reduce pain caused by nerve related pain conditions.

BACKGROUND

Many acute and chronic conditions cause pain, wounds, infections, or other injuries to the human body. Various medical devices are configured to apply electrotherapy or radiation therapy, or heat therapy to one or more areas of a patient's body to reduce pain. Conventional devices include electrodes configured to be secured relative to an area of the patient's body and deliver the electrotherapy to that area of the patient's body. Conventional devices further include wires or leads that connect a power source, such as a battery, to the electrodes. The wires or leads may become tangled or damaged during use of the medical device thereby decreasing the convenience and lifespan of the medical device.

SUMMARY

In accordance with an aspect of the disclosure, the present application discloses a transcutaneous electronic nerve stimulation device configured to be positioned adjacent to a portion of a patient's body and further configured to provide therapy to the portion of the patient's body. The transcutaneous electronic nerve stimulation device includes a control unit assembly including a power source. The transcutaneous electronic nerve stimulation device further includes a therapy plate electrically coupled to the power source. The therapy plate includes an electrical source configured to deliver electrical stimulation to the portion of the patient's body, a heat source configured to deliver heat to the portion of the patient's body, and a radiation source configured to deliver radiation to the portion of the patient's body. The transcutaneous electronic nerve stimulation device further includes a rigid connector electrically coupling the therapy plate to the power source such that the therapy plate is fixed relative to the power source.

In accordance with another aspect of the disclosure, the present application discloses a transcutaneous electronic nerve stimulation device configured to be positioned adjacent to a portion of a patient's body and further configured to provide therapy to the portion of the patient's body. The transcutaneous electronic nerve stimulation device includes a control unit assembly including a user interface and a power source, and a therapy plate electrically coupled to the power source. The therapy plate includes an electrical source configured to deliver electrical stimulation to the portion of the patient's body, a heat source configured to deliver heat to the portion of the patient's body, and a radiation source configured to deliver radiation to the portion of the patient's body. The user interface is configured to receive input to toggle on and toggle off delivery of the electrical stimulation, the heat, the radiation, or any combination thereof to the portion of the patient.

According to another aspect of the disclosure, the application discloses a method of assembling a transcutaneous electronic nerve stimulation device configured to be positioned adjacent to a portion of a patient's body and further configured to provide therapy to the portion of the patient's body. The method includes the steps of positioning an insulating layer of a therapy plate of the transcutaneous electronic nerve stimulation device between an electrical source of the therapy plate and a radiation source of the therapy plate, and after the positioning step, electrically and rigidly coupling the therapy plate to a power source of a control unit assembly of the transcutaneous electronic nerve stimulation device.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 1 is an isometric view of a transcutaneous electronic nerve stimulation device according to an aspect of the disclosure;

FIG. 2 is an exploded isometric view of the transcutaneous electronic nerve stimulation device illustrated in FIG. 1;

DETAILED DESCRIPTION OF ILLUSTRATIVE EMBODIMENTS

Figure 4:
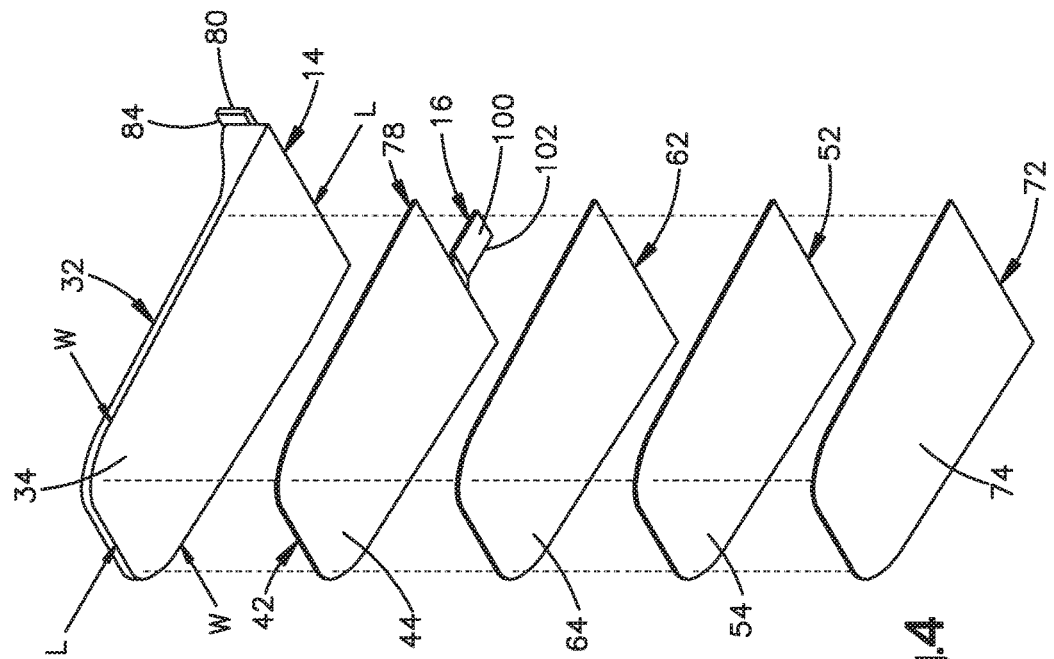
FIG. 4 is an exploded bottom isometric view of the therapy plate illustrated in FIG. 3.

Certain terminology is used in the following description for convenience only and is not limiting. The words "lower" and "upper" designate directions in the drawings to which reference is made. Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure each include up to an entirety of the structure. Certain features of the disclosure which are described herein in the context of separate embodiments may also be provided in combination in a single embodiment. Conversely, various features of the disclosure that are described in the context of a single embodiment may also be provided separately or in any subcombination.

Referring to FIGS. 1 and 2, a transcutaneous electronic nerve stimulation ("TENS") device is configured to be positioned adjacent to a portion of a person's, for example a patient's or a user's body, and further configured to provide therapy to the portion of the patient's body. According to one aspect of the disclosure, the TENS device 10 includes a control unit assembly 12, a therapy plate 14, and a connector 16 electrically coupling the therapy plate 14 to a power source 18 of the TENS device 10. As shown in the illustrated embodiment the TENS device 10 may include a plurality of therapy plates 14 including at least a first therapy plate 14a and a second therapy plate 14b. It will be understood that the description of the therapy plate 14 herein is applicable to each of the plurality of therapy plates 14 of the TENS device 10.

In use, the TENS device 10 is configured to be positioned relative to a portion of a patient's body such that the therapy plate 14 is positioned to deliver electrotherapy, heat therapy, radiation therapy, or any combination thereof to the portion of the patient's body. The control unit assembly 12, is configured to receive an input and then cause the therapy plate 14 to deliver electrotherapy, heat therapy, radiation therapy, or any combination thereof to the portion of the patient's body.

According to one aspect of the disclosure, the TENS device 10 includes the power source 18, a processor 20, and a user interface 22. The user interface 22 may be configured to receive input to toggle on and toggle off delivery of the electrotherapy, the heat therapy, the radiation therapy, or any combination thereof to the portion of the patient's body. The user interface 22 may include one or more controls 24 physically carried by the TENS device 10. As shown in the illustrated embodiment, the control unit assembly 12 includes a housing 26 that supports the one or more controls 24. The one or more controls 24 may include buttons, knobs, switches, other types of physical input apparatuses, or any combination thereof. The housing 26 may be a single, monolithic member, or may include a plurality of portions for example first portion 27a and second portion 27b configured to be connected to form the housing 26.

According to one aspect of the disclosure, the user interface 22 of the TENS device 10 may be remote from both the user input assembly 12 and the therapy plate 14. For example, the user interface 22 may include an application on a cellular phone which can receive input from a user of the TENS device 10 and transfer the input wirelessly to the TENS device 10. According to one aspect of the disclosure, the user interface 22 may include one or more controls 24 physically carried by the TENS device 10, and may also be configured to receive input from a device that is remote from both the user input assembly 12 and the therapy plate 14.

The processor 20 is operably connected to the user interface 22 such that an input into the user interface 22 is converted by the processor 20 into instructions that are sent to the power source 18. For example, an input into the user interface 22 to toggle on radiation therapy may be converted into an instruction to power source 18 to deliver power to the therapy plate 14 thereby causing the therapy plate 14 to deliver radiation therapy to the portion of the patient. The processor 20 may include a circuit board 28, as shown in the illustrated embodiment.

The power source 18 is configured to store a source of power, for example electricity, until an instruction is received from the processor 20 to deliver at least a portion of the stored power to the therapy plate 14. As shown in the illustrated embodiment, the power source 18 may include a battery 30. According to one aspect of the disclosure, the power source 18 and the processor 20 are each supported by the control unit assembly 12, for example at least partially enclosed with the housing 26.

Figure 3:
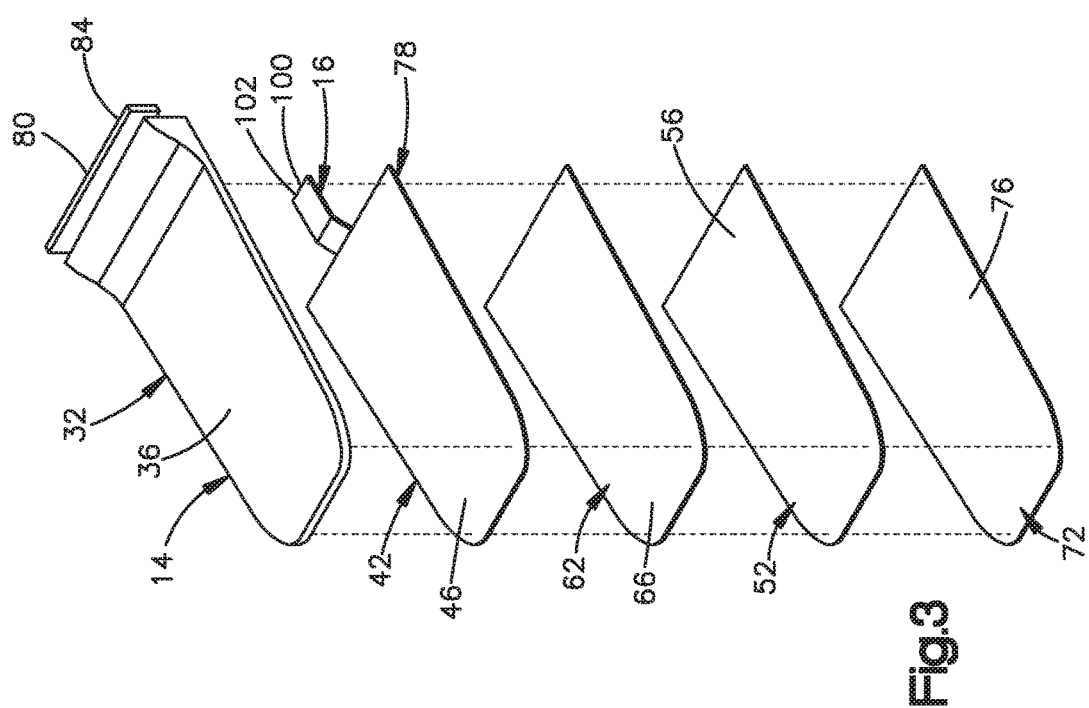
FIG. 3 is an exploded top isometric view of a therapy plate of the transcutaneous electronic nerve stimulation device illustrated in FIG. 1, according to one aspect of the disclosure.

Referring to FIGS. 3 and 4, the therapy plate 14 is configured to deliver electrical stimulation, heat, radiation, or any combination thereof either in sequence or simultaneously to the portion of the patient's body. As shown in the illustrated embodiment, the therapy plate 14 may include a protective housing 32. The protective housing 32 includes a first surface 34 that faces toward the patient's body when the therapy plate 14 is providing therapy to the portion of the patient's body, and a second surface 36 that faces away from the portion of the patient's body when the therapy plate 14 is providing therapy to the portion of the patient's body. The protective housing 32 may be configured to at least partially block electrical stimulation, heat, radiation, or any combination thereof produced by the therapy plate 14 from being delivered in a direction away from the portion of the patient's body, for example, into an environment surrounding the patient.

The therapy plate 14 can include one of a variety of shapes. For example, the therapy plate 14 may define a length L measured along a first direction, and the therapy plate 14 may further define a width W measured along a second direction perpendicular to the first direction. When the therapy plate 14 is coupled to the input assembly 12 as shown in FIG. 1, the first direction may extend away from the input assembly 12. According to one embodiment, the therapy plate 14 is configured such that the length L is greater than the width W. According to another embodiment, the therapy plate 14 is configured such that the length L is less than the width W. According to another embodiment, the therapy plate 14 is configured such that the length L is about equal to the width W. The therapy plate 14 may define a shape that includes a polygon, an irregular shape, and a shape that is configured to conform to a certain part of a patient's anatomy, for example an arm.

According to one aspect of the disclosure, the TENS device 10 may include the first therapy plate 14a which has a first shape, and the second therapy plate 14b that has a second shape that is the same as the first shape. According to another aspect of the disclosure, the first therapy plate 14a has a first shape, the second therapy plate 14 has a second shape, and the first shape is different than the second shape.

The therapy plate 14 may include a radiation source 42 that is configured to generate and deliver radiation therapy to the portion of the patient's body. The radiation source 42 may include a first surface 44 that faces toward the patient's body when the therapy plate 14 is providing therapy to the portion of the patient's body, and a second surface 46 that faces away from the portion of the patient's body when the therapy plate 14 is providing therapy to the portion of the patient's body.

According to one aspect of the disclosure, the second surface 46 of the radiation source 42 faces the first surface 34 of the protective housing 32 and away from the portion of the patient's body when the therapy plate 14 is providing therapy to the portion of the patient's body, and the first surface 44 of the radiation source 42 faces toward the patient's body when the therapy plate 14 is providing therapy to the portion of the patient's body.

The radiation source 42, according to one aspect of the disclosure, is configured to deliver far-infrared radiation (FIR). The radiation source 42 may be configured to deliver, for example emit, radiation within a range of wavelengths. According to one aspect of the disclosure, the radiation source 42 may be configured to emit between about 4 micrometers and about 16 micrometers of FIR to the portion of the patient's body. The radiation source 42 may include a porous carbon fiber, for example a polyacrylonitrile-based carbon fiber.

Referring to FIGS. 1 to 4, the radiation source 42 may be configured to be toggled on, for example when an input is received by the control unit assembly 12, thereby causing the radiation source 42 to deliver radiation to the portion of the patient's body. The radiation source 42 may further be configured to be toggled off, for example when another input is received by the control unit assembly 12, thereby causing the radiation source 42 to stop delivering radiation to the portion of the patient's body.

According to one aspect of the disclosure, a method of assembling the TENS device 10 includes the step of exposing polyacrylonitrile-based carbon fiber to a temperature above about 1000 degrees Celsius, thereby producing the radiation source 42. According to one aspect of the disclosure the temperature is above about 1100 degrees Celsius. According to one aspect of the disclosure the radiation source 42 includes bamboo charcoal, doped bio-ceramic materials, or both.

Referring to FIGS. 3 and 4, the therapy plate 14 may include an electrical source 52 that is configured to generate and deliver electrical therapy, for example electrical stimulation, to the portion of the patient's body. The electrical source 52 may include a first surface 54 that faces toward the patient's body when the therapy plate 14 is providing therapy to the portion of the patient's body, and a second surface 56 that faces away from the portion of the patient's body when the therapy plate 14 is providing therapy to the portion of the patient's body.

According to one aspect of the disclosure, the second surface 56 of the electrical source 52 faces in a direction toward the first surface 44 of the radiation source 42 and away from the portion of the patient's body when the therapy plate 14 is providing therapy to the portion of the patient's body, and the first surface 54 of the electrical source 52 faces toward the patient's body when the therapy plate 14 is providing therapy to the portion of the patient's body.

The electrical source 52, according to one aspect of the disclosure, is configured to deliver low-frequency electrical stimulation. The low-frequency stimulation may be below about 200 Hz of alternating current. According to one aspect of the disclosure the low-frequency stimulation is between about 10 Hz and about 30 Hz of alternating current. The electrical source 52 may be configured to deliver low-frequency stimulation in a range that mitigates swelling of muscle tissues and improves blood circulation to help treat muscle fatigue.

The electrical source 52, according to one aspect of the disclosure, is configured to deliver mid-frequency electrical stimulation. The mid-frequency stimulation may between about 1 kHz and about 10 kHz of alternating current. The electrical source 52 may be configured to deliver mid-frequency stimulation in a range that penetrates the portion of the body deeper than the low-frequency electrical stimulation.

The electrical source 52, according to one aspect of the disclosure, is configured to deliver modulated mid-frequency electrical stimulation. The modulated mid-frequency electrical stimulation includes alternating between both the low-frequency electrical stimulation and the mid-frequency electrical stimulation. According to one aspect of the disclosure, the electrical source 52 is configured to deliver low-frequency electrical stimulation, mid-frequency electrical stimulation, modulated mid-frequency electrical stimulation, or any combination thereof.

The inclusion of an electrical source 52 that is configured to deliver modulated mid-frequency electrical stimulation on the therapy plate 14 which is configured to be rigidly connected to the power source 18 such that the therapy plate 14 is fixed relative to the power source 18, as will be described in greater detail below, provides greater flexibility in the type of therapy provided by the TENS device 10 while still providing enhanced user efficiency compared to larger desktop or other TENS deices with flexible wire connections between the therapy plate 14 and the power source 18.

Referring to FIGS. 1 to 4, the electrical source 52 may be configured to be toggled on, for example when an input is received by the control unit assembly 12, thereby causing the electrical source 52 to deliver electrical stimulation to the portion of the patient's body. The electrical source 52 may further be configured to be toggled off, for example when another input is received by the control unit assembly 12, thereby causing the electrical source 52 to stop delivering electrical stimulation to the portion of the patient's body.

According to one aspect of the disclosure, a method of assembling the TENS device 10 includes the step of screen printing conductive materials, doping conductive materials, or both, thereby producing the electrical source 52.

Referring to FIGS. 3 and 4, the therapy plate 14 may include insulation 62 that is configured to prevent interference, for example electrical interference, between the radiation source 42 and the electrical source 52. The insulation 62 may include a first surface 64 that faces toward the electrical source 52, for example the second side 56 of the electrical source 52, and the insulation 62 may further include a second surface 66 that faces toward the radiation source 42, for example the first side 44 of the radiation source 42. As shown in the illustrated embodiment, the insulation 62 may be configured such that all paths (along a straight line) from the radiation source 42 to the electrical source 52 pass through the insulation 62.

The therapy plate 14 may further include a conductor 72 that is configured to conduct the electrical therapy from the electrical source 52 to the portion of the patient's body. The conductor 72 may include a conductive gel that is applicable to the electrical source 52, for example the first side 54 of the electrical source. The conductor 72 may be positioned between the portion of the patient's body and the electrical source 52 such that the conductor is in direct contact with both the patient's body and the electrical source 52. The conductor 72 may include a first side 74 that directly contacts the patient's body when the therapy plate 14 is providing therapy to the portion of the patient's body, and a second surface 76 that faces away from the portion of the patient's body and directly contact's the electrical source 52 when the therapy plate 14 is providing therapy to the portion of the patient's body.

According to one aspect of the disclosure, the therapy plate 14 includes the protective housing 32, the radiation source 42, the electrical source 52, the insulation 62, the conductor 72, or any combination thereof. According to one aspect of the disclosure, the radiation source 42 is positioned between the protective housing 32 and the electrical source 52, the insulation 62 is positioned between the radiation source 42 and the electrical source 52, the electrical source 52 is positioned between the insulation 62 and the conductor 72, or any combination thereof.

The therapy plate 14 may include a heat source 78 that is configured to generate and deliver heat to the portion of the patient's body. According to one aspect of the disclosure, the heat source 78 is separate from both the radiation source 42 and the electrical source 52. As shown in the illustrated embodiment, the heat source 78 may be radiation source 42, the electrical source 52, or both, such that, for example, the radiation source 42 is configured to deliver both radiation therapy and heat to the portion of the patient's body. According to one aspect of the disclosure the heat source 78 includes the porous carbon fiber of the radiation source 42 such that the heat source 78 does not produce electromagnetic radiation.

Referring to FIGS. 1 to 4, the heat source 78 may be configured to be toggled on, for example when an input is received by the control unit assembly 12, thereby causing the heat source 78 to deliver heat to the portion of the patient's body. The heat source 78 may further be configured to be toggled off, for example when another input is received by the control unit assembly 12, thereby causing the heat source 78 to stop delivering heat to the portion of the patient's body.

Each of the therapy plates 14 of the TENS device 10 may be configured to receive input, from the user interface 22, to adjust the therapy provided by the therapy plate 14 to the portion of the patient's body. For example, the therapy plate 14 may be configured to generate and deliver only one of electrical stimulation, radiation, and heat to the portion of the patient's body at a time. According to another aspect of the disclosure, the therapy plate 14 may be configured to generate and deliver electrical stimulation, radiation, heat, or any combination thereof to the portion of the patient's body simultaneously.

According to one aspect of the disclosure, the user interface 22 of the TENS device 10 is configured to receive inputs that adjust and select the frequency, current, voltage, waveform, pulse width, or any combination thereof, of the electrical stimulation. According to one aspect of the disclosure, the TENS device 10 is configured such that adjustment of the temperature of the radiation source 42 may result in adjustment of the radiation strength, for example increasing the temperature of the radiation source may increase the strength of the radiation therapy that is provided to the patient's body.

Referring to FIGS. 1 to 4, the therapy plate 14 includes an attachment mechanism 80 configured to secure the therapy plate 14 relative to the control unit assembly 12. According to one aspect of the disclosure the control unit assembly 12 may include an attachment mechanism 82 that cooperates with the attachment mechanism 80 of the therapy plate 14 to secure the therapy plate 14 relative to the control unit assembly 12. As shown in the illustrated embodiment, one of the attachment mechanism 80 and the attachment mechanism 82 may include a projection 84 and the other of the attachment mechanism 80 and the attachment mechanism 82 may include a corresponding recess 86. According to another embodiment, the attachment mechanism 80 may include an adhesive, magnetic materials, or both.

According to one aspect of the disclosure, the therapy plate 14 is removably secured to the control unit assembly 12 such that when the TENS device 10 is not providing therapy to the patient, the therapy plate 14 can be removed from the control unit assembly 12 without plastically deforming either of the therapy plate 14 and the control unit assembly 12, allowing the therapy plate 14 to be cleaned, repaired, replaced, or any combination thereof, and then the therapy plate 14 can be re-secured to the control unit assembly 12 without plastically deforming either of the therapy plate 14 and the control unit assembly 12. As shown in the illustrated embodiment, the attachment mechanism 80 may be carried by, for example monolithic with, the protective housing 32.

According to another aspect of the disclosure, the therapy plate 14 is permanently secured relative to the control unit assembly 12 such that the therapy plate 14 cannot be removed from the control unit assembly without plastically deforming at least one of the therapy plate 14 and the control unit assembly 12.

According to one aspect of the disclosure, the connector 16 is a rigid connector 100 configured to electrically couple the therapy plate 14 to the power source 18 such that the therapy plate 14 is fixed relative to the power source 18. Accordingly, the TENS device 10 may be devoid of a flexible connector that electrically couples the therapy plate 14 to the power source 18 such that the therapy plate 14 is movable relative to the power source 18. While the use of the rigid connector 100 to electrically couple the therapy plate 14 to the power source 18 may decrease he flexibility of choices for positioning the therapy plate 14 relative to the control unit assembly 12, the use of the rigid connector 100 may also increase the convenience and efficiency of using the TENS device 10 as the rigid connector 100 cannot become tangled or damaged by objects in the surrounding environment. Use of a flexible connector, such as an electrical wire, may result in a device that is more prone to damage or breakage as the flexible connector gets tangled on objects in the surrounding environment.

The rigid connector 100 may include a corresponding pair of bridge connectors, for example a male bridge connector 102 and a female bridge connector 104, configured to cooperate to define a portion of an electrical connection between the power source 18 and the therapy plate 14. According to one aspect of the disclosure, the rigid connector 100 extends from the power source 18 to the therapy plate 14 such that an electrical circuit is defined that is devoid of any portion that is elastically deformable. As shown in the illustrated embodiment the male bridge connector 102 my be carried by the therapy plate 14, for example the radiation source 42, and the female bridge connector 104 may be carried by the control unit assembly 12, for example the circuit board 28. Although described herein as a pair of bridge connectors, the rigid connector 100 may include other types connectors, such as pogopins, or other types varieties of male-female connectors.

The rigid connector 100 may include a portion that is carried by the radiation source 42, the electrical source 52, the heat source 78, or any combination thereof. As shown in the illustrated embodiment, the male bridge connector 102 may be directly coupled to the radiation source 42. Alternatively the rigid connector 100 may include a plurality of male bridge connectors 102, for example one directly coupled to the radiation source 42 and another coupled to the electrical source. The TENS device 10 may include a plurality of rigid connectors 100, for example at least one rigid connector 100 for each therapy plate 14 of the TENS device 10.

According to one aspect of the disclosure, the TENS device 10 may be part of a kit that includes the control unit assembly 12, a first set of one or more therapy plates 14 each having a first shape, a second set of one or more therapy plate 14 each having a second shape that is different than the first shape, and at least one connector 16 configured to electrically couple any one of the first set of one or more therapy plates 14 and any one of the second set of one or more therapy plates 14 with the power source 18.

According to one aspect of the disclosure a method of assembling the TENS device 10 includes the steps of positioning the insulation 62 of the therapy plate 14 between the electrical source 52 and the radiation source 42, and after the positioning step, electrically and rigidly coupling the therapy plate 14 to the power source 18 of the TENS device 10 such that the therapy plate is fixed relative to the power source. The method may further include prior to the positioning step, the step of exposing polyacrylonitrile-based carbon fiber to temperatures above about 1000 degrees Celsius, thereby producing the radiation source. The electrically and rigidly coupling step may include the step of attaching a male bridge connector of one of the therapy plate and the control unit assembly to a female bridge connector of the other of the therapy plate and the control unit assembly.

It will be appreciated that the foregoing description provides examples of the disclosed device and methods of use and assembly. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range including the stated ends of the range, unless otherwise indicated herein, and each separate value is incorporated into the specification as if it were individually recited herein. All methods described herein can be performed in any suitable order unless otherwise indicated herein or otherwise clearly contradicted by context.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A transcutaneous electronic nerve stimulation device configured to be positioned adjacent to a portion of a patient's body and further configured to provide therapy to the portion of the patient's body, the transcutaneous electronic nerve stimulation device comprising:
    a control unit assembly including:
        an attachment mechanism configured to include a recess;
        a user interface; and
        a power source;
    a therapy plate electrically coupled to the power source, the therapy plate including:
        an electrical source configured to deliver electrical stimulation to the portion of the patient's body;
        a radiation source configured to deliver radiation to the portion of the patient's body;
    a rigid connector electrically coupling the therapy plate to the power source such that the therapy plate is fixed relative to the power source; and
    an attachment mechanism configured to include a projection, and to cooperate with the recess of the attachment mechanism of the control unit assembly:
    wherein the user interface is configured to receive input to toggle on and toggle off delivery of the electrical stimulation, the heat, the radiation, or any combination thereof to the portion of the patient's body;
    wherein:
    the electrical source includes a first side configured to face the portion of the patient's body, and a second side opposite the first side;
    the radiation source includes a first side configured to face the second side of the electrical source, and a second side opposite the first side of the radiation source; and
    the therapy plate includes an insulating layer positioned between the second side of the electrical source and the first side of the radiation source.

2. The transcutaneous electronic nerve stimulation device of claim 1, wherein the transcutaneous electronic nerve stimulation device is configured to deliver: 1) electrical stimulation to the portion of the patient's body, 2) heat to the portion of the patient's body, 3) radiation to the portion of the patient's body, 4) or any combination thereof simultaneously to the portion of the patient's body.

3. The transcutaneous electronic nerve stimulation device of claim 1, wherein the radiation source includes a far infrared radiation source.

4. The transcutaneous electronic nerve stimulation device of claim 3, wherein the far infrared radiation source includes a layer of porous carbon fiber.

5. The transcutaneous electronic nerve stimulation device of claim 1, wherein the therapy plate includes a conductive layer positioned between the first side of the electrical source and the portion of the patient's body, and the therapy plate further includes a protecting layer that faces the second side of the radiation source.

6. The transcutaneous electronic nerve stimulation device of claim 1, wherein the therapy plate is a first therapy plate, the transcutaneous electronic nerve stimulation device further comprising a second therapy plate, both the first and second therapy plates being electrically and rigidly coupled to the power source such that both the first and second therapy plates are fixed relative to the power source, the second therapy plate including:
    an electrical source configured to deliver electrical stimulation to the patient; and
    a radiation source configured to deliver radiation to the patient.

* * * * *